United States Patent
Wu et al.

(10) Patent No.: US 9,416,631 B2
(45) Date of Patent: Aug. 16, 2016

(54) MODELING FLUID DISPLACEMENT IN A WELL SYSTEM ENVIRONMENT

(71) Applicant: HALLIBURTON ENERGY SERVICES, INC., Houston, TX (US)

(72) Inventors: Hongfei Wu, Katy, TX (US); Srinath Madasu, Houston, TX (US); Avi Lin, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 14/377,453

(22) PCT Filed: Feb. 11, 2014

(86) PCT No.: PCT/US2014/015882
§ 371 (c)(1),
(2) Date: Aug. 7, 2014

(87) PCT Pub. No.: WO2015/030863
PCT Pub. Date: Mar. 5, 2015

(65) Prior Publication Data
US 2015/0066457 A1 Mar. 5, 2015

Related U.S. Application Data

(60) Provisional application No. 61/870,644, filed on Aug. 27, 2013.

(51) Int. Cl.
*G06G 7/48* (2006.01)
*E21B 43/00* (2006.01)
(Continued)

(52) U.S. Cl.
CPC ............ *E21B 43/00* (2013.01); *G06F 17/5009* (2013.01); *G01N 2013/003* (2013.01); *G06F 2217/16* (2013.01)

(58) Field of Classification Search
CPC .................................................. G01N 2013/003
USPC ........................................................... 703/10
See application file for complete search history.

(56) References Cited

U.S. PATENT DOCUMENTS 7,229,593 B1 6/2007 Ho
2009/0272528 A1 11/2009 Voelker

FOREIGN PATENT DOCUMENTS

WO WO2012092013 7/2012

OTHER PUBLICATIONS

Zimmermann & Homsy: Viscous fingering in miscible displacements: Unification of effects of viscosity contrast, anisotropic dispersion & velocity dependence of dispersion on nonlinear finger propagation; Physics of Fluids A: Fluid Dynamics (1989-1993) 4, pp. 2348-2359 (1992).*

(Continued)

*Primary Examiner* — Hugh Jones
(74) *Attorney, Agent, or Firm* — Craig W. Roddy; Fish & Richardson P.C.

(57) ABSTRACT

In some aspects, a one-dimensional flow model is generated. The one-dimensional flow model can represent flow of a first fluid and a second fluid in a flow path in a well system environment. The one-dimensional flow model comprises an effective diffusion coefficient model for a composite fluid volume comprising the first and second fluids. The effective diffusion coefficient model calculates an effective diffusion coefficient for the composite fluid volume based on a difference between the respective densities and viscosities of the first fluid and the second fluid.

17 Claims, 7 Drawing Sheets

(51) Int. Cl.
*G06F 17/50* (2006.01)
*G01N 13/00* (2006.01)

(56) References Cited

OTHER PUBLICATIONS

Manickam: Viscous fingering in miscible displacements in porous media with non-monotonic viscosity profiles; PhD Thesis; Stanford; 1994; 154 pages.*
Manickam and Homsy: Stability of miscible displacements in porous media with non-monotonic viscosity Profiles; Physics of Fluids A: Fluid Dynamics (1989-1993) 5, pp. 1356-1367 (1993).*
Pelce: New Visions on Form and Growth (Chapter 6); Oxford U Press; 2000; 34 pages.*
Sorbie et al. Experimental Testing of Mobility Predictions in Averaged Models of Viscous Fingering, SPE 22617, 1991; pp. 255-270.*
Subramanian: Miscible Dispersion; AIChEMI Modular Instruction Series C: Transport, vol. 6: Transport Phenomena—Special Topics (R.J. Gordon, Ed.), AIChE; 1986; pp. 9-16.*
Darcy's law—Wikipedia, the free encyclopedia; Feb. 2012; 5 pages.*
Neuman: Theoretical Derivation of Darcy's Law; Acta Mechanica 25, 153-170 (1977).*
Bacri et al.: Miscible viscous fingering: Experiments versus continuum approach; Physics of Fluids A: Fluid Dynamics (1989-1993) 4, 1611 (1992).*
Authorized Officer Ji Myong Nho, PCT International Search Report and Written Opinion of the International Searching Authority, PCT/US2014/015882, Jun. 26, 2014, 9 pages.
Chao-Ying Jiao et al., "An Experimental Study of Miscible Displacements in Porous Media with Variation of Fluid Density and Viscosity", Transport in Porous Media, vol. 54, Issue 2, pp. 125-144, Feb. 2004, 20 pages.
Yusuke Kirino et al., "Effect of Density-Driven Flow on the Through-Diffusion Experiment", Journal of Contaminant Hydrology, vol. 106, Issues 3-4, pp. 169-172, May 12, 2009, 7 pages.
Anderson et al., "Diffuse-Interface Methods in Fluid Mechanics", Annu. Ref. Fluid Mech. Copyright 1998, 27 pages.
Liu et al., "A Phase Field Model for the Mixture of Two Incompressible Fluids and its Approximation by a Fourier-Spectral Method", Science Direct, Published in 2003, 18 pages.

Buckley et al., "Mechanism of Fluid Displacement in Sands", Feb. 1941, 10 pages. New York Meeting (public talk).
Doster et al., "Generalized Buckley—Leverett Theory for Two-Phase Flow in Porous Media", Published in 2011, 33 pages.
Haberman, "The Efficiency of Miscible Displacement as a Function of Mobility Ratio", Jul. 11, 1960, 9 pages. SPE 1540—G.
Hirt et al., "Volume of Fluid (VOF) Method for the Dynamics of Free Boundaries", Journal of Computational Physics, vol. 39, 25 pages. 1981.
Homsy, "Viscous Fingering in Porous Media", Ann. Rev. Fluid Mech., Published in 1987, 41 pages.
Kirino et al., "Effect of Density-Driven Flow on the Through-Diffusion Experiment", Journal of Contaminant Hydrology, vol. 106, published in 2009, 7 pages.
Mishra et al., "Influence of Double Diffusive Effects on Miscible Viscous Fingering", Nov. 8, 2010, 4 pages. Phys Rev Lett.
Osher, "Fronts Propagating with Curvature—Dependent Speed: Algorithms Based on Hamilton—Jacobi Formulations", Journal of Computational Physics, vol. 79, published in 1988, 38 pages.
Smirnov et al., "Instability and Mixing Flux in Frontal Displacement of Viscous Fluids from Porous Media", Published in 2005, 21 pages.
Taylor, "Dispersion of Soluble Matter in Solvent Flowing Slowly through a Tube", Proceedings of the Royal Society of London, vol. 219, No. 1137, Aug. 25, 1953, 19 pages.
Unverdi et al., "A Front-Tracking Method for Viscous, Incompressible Multi-Fluid Flows", Journal of Computational Physics, vol. 100, published in 1992, 13 pages.
Upchurch et al., "Miscible Porous Media Displacements Driven by Non-Vertical Injection Wells", J. Fluid Mech. vol. 607, Published in 2008, 24 pages.
Yue et al., "A Diffuse-Interface Method for Simulating Two-Phase Flows of Complex Fluids", J. Fluid Mech. vol. 515, published in 2004, 25 pages.
Chikhliwala et al. "Numerical Study of the Linear Stability of Immiscible Displacement Processes in Porous Media", Transport in Porous Media 3, Published in 1988, pp. 257-276.
Tryggvason et al. "Numerical Experiments on Hele Shaw Flow with a Sharp Interface", J. Fluid Mech. vol. 136, Published in 1983, pp. 1-30.
PCT International Preliminary Report on Patentability, PCT/US2014/015882, Mar. 10, 2016, 6 pages.

* cited by examiner

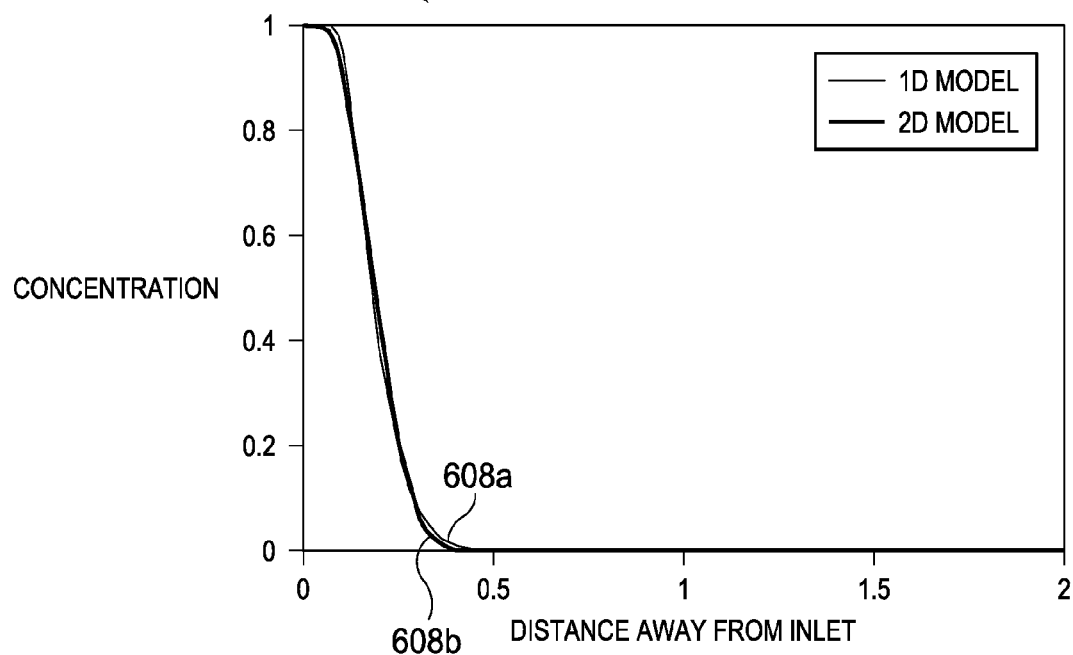
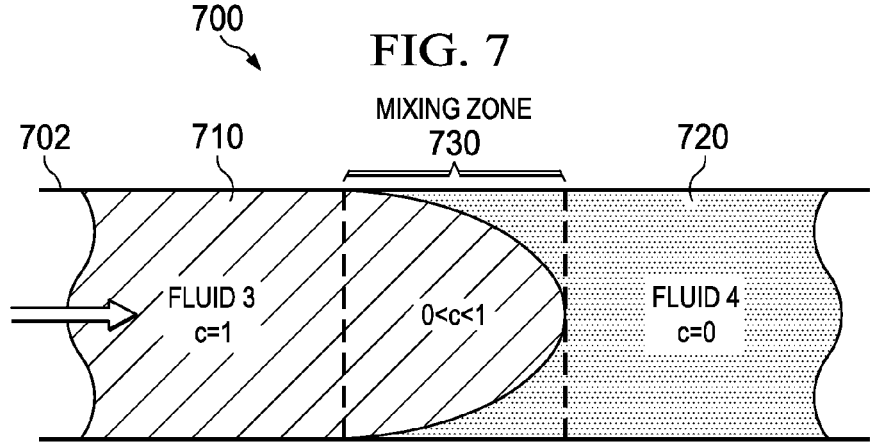

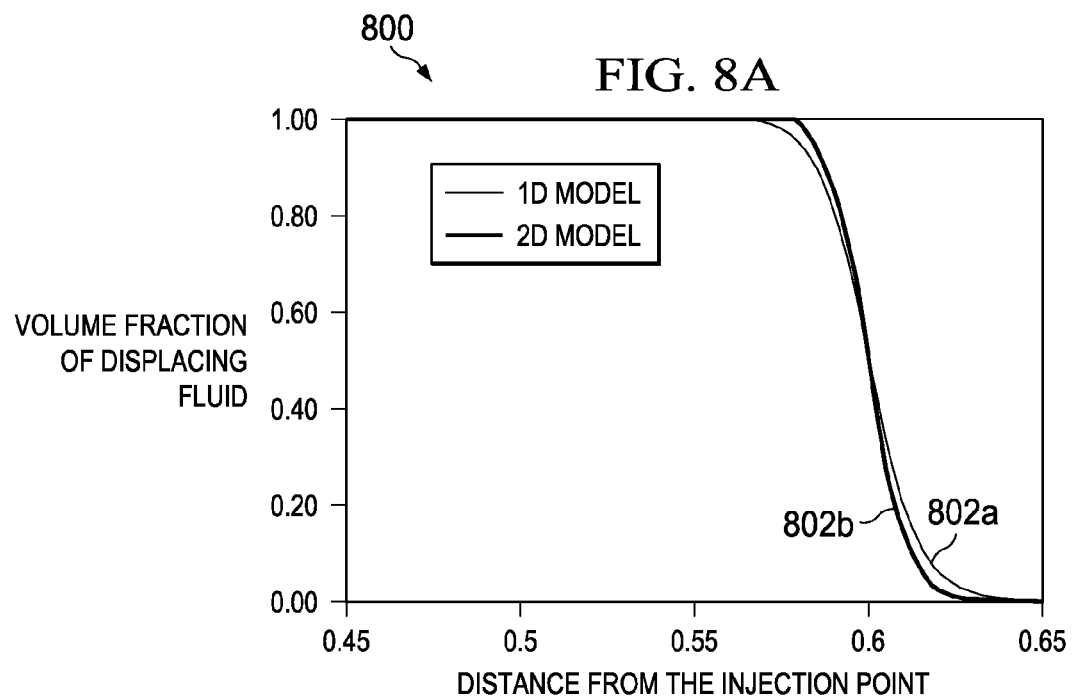
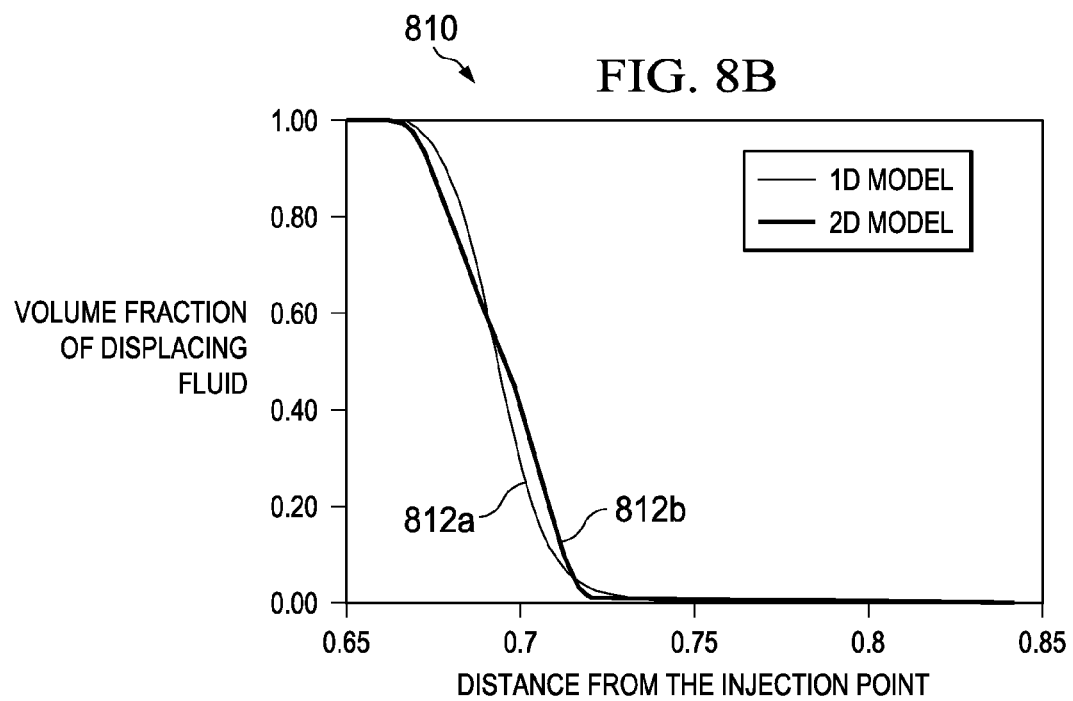

__US 9,416,631 B2__

MODELING FLUID DISPLACEMENT IN A WELL SYSTEM ENVIRONMENT

CLAIM OF PRIORITY

This application is a U.S. National Phase application under 35 U.S.C. §371 and claims the benefit of priority to PCT Application Serial No. PCT/US2014/015882, filed on Feb. 11, 2014 and entitled "Modeling Fluid Displacement in a Well System Environment", which claims the benefit of priority to U.S. Provisional Application Ser. No. 61/870,644, filed on Aug. 27, 2013, and entitled "Modeling Proppant Flow and Fluid Displacement in a Well System Environment", the entire contents of both are hereby incorporated by reference.

BACKGROUND

The following description relates to modeling fluid displacement, for example, in a simulation of fluid flow in a well system environment.

Fluid models have been used to simulate fluid flow in well systems and other environments. For example, fluid models have been used to model fluid flow during fracture treatments applied to subterranean rock formations. During a conventional fracture treatment, pressurized fluid is communicated from a wellbore into the reservoir at high pressure, and the pressurized fluid can fracture the rock formation.

DESCRIPTION OF DRAWINGS

FIGS. 6A, 6B, 6C, and 6D are plots showing data from example numerical simulations.

FIG. 7 is a diagram showing an example of immiscible fluids in a wellbore.

FIGS. 8A and 8B are plots showing data from example numerical simulations.

Like reference symbols in the various drawings indicate like elements.

DETAILED DESCRIPTION

Fluid flow models can be used to analyze fluid flow, for example, in a well system environment (e.g., in a wellbore, a fracture network, within the reservoir rock matrix, in a well system tool, etc.) or other environments. In some environments, the fluid flow is unsteady and multi-dimensional (e.g., three-dimensional or at least two-dimensional). For example, in some types of fractures, the dominant flow is two-dimensional, and includes transient behaviors. In some instances, two- or three-dimensional flow can be described by a one-dimensional flow model, for example, by integrating the governing flow equations over the cross-section of the two- or three-dimensional flow path. In some cases, the resulting equations include nonlinear partial differential equations that can be solved using finite difference, finite volume, or finite element methods. In some cases, the use of one-dimensional flow models can reduce computational costs, and allow for faster or more computationally efficient simulations. In some instances, a flow model can be used to perform numerical simulations in real time, for example, during a fracture treatment or during another well system activity.

In some cases, a fluid flow model models multiple fluids in a well system environment, for example, the displacement of one fluid by another fluid. Fluid displacement may occur when a sequence of moving fluids physically interact with each other. Fluid displacement can occur, for example, in a well system environment in a process such as hydraulic fracturing, which involves the injection of fluids at different pumping or perforation stages. Displacement can occur where the injected fluids interact with each other or with native fluids in the reservoir.

In a well system environment, multiple distinct fluids can exist in separate physical domains, for example, in separate parts of a flow path. In an intermediate region (e.g., at a fluid interface or mixing zone), the distinct fluids may coexist in a common domain. For example, the fluids may form a composite fluid volume in the intermediate region. In some instances, one of the fluids displaces the other fluid within the flow path, causing the intermediate region to move along the flow path.

The fluid properties of the composite fluid in the intermediate region can be distinct from the properties of the separate constituent fluids, and numerical simulations can account for the distinct fluid properties of the composite fluid. The fluids in the intermediate region may be miscible (e.g., fully or partially miscible) or immiscible. Miscible fluids can combine into a substantially homogenous solution. For example, certain alcohols and water are miscible. Some fluids are partially miscible, for example, when they are not fully soluble but each fluid near the interface holds the other fluid. For example, water and phenol are partially miscible. Immiscible fluids are not mutually soluble. For example, oil and water are immiscible.

Figure 1:
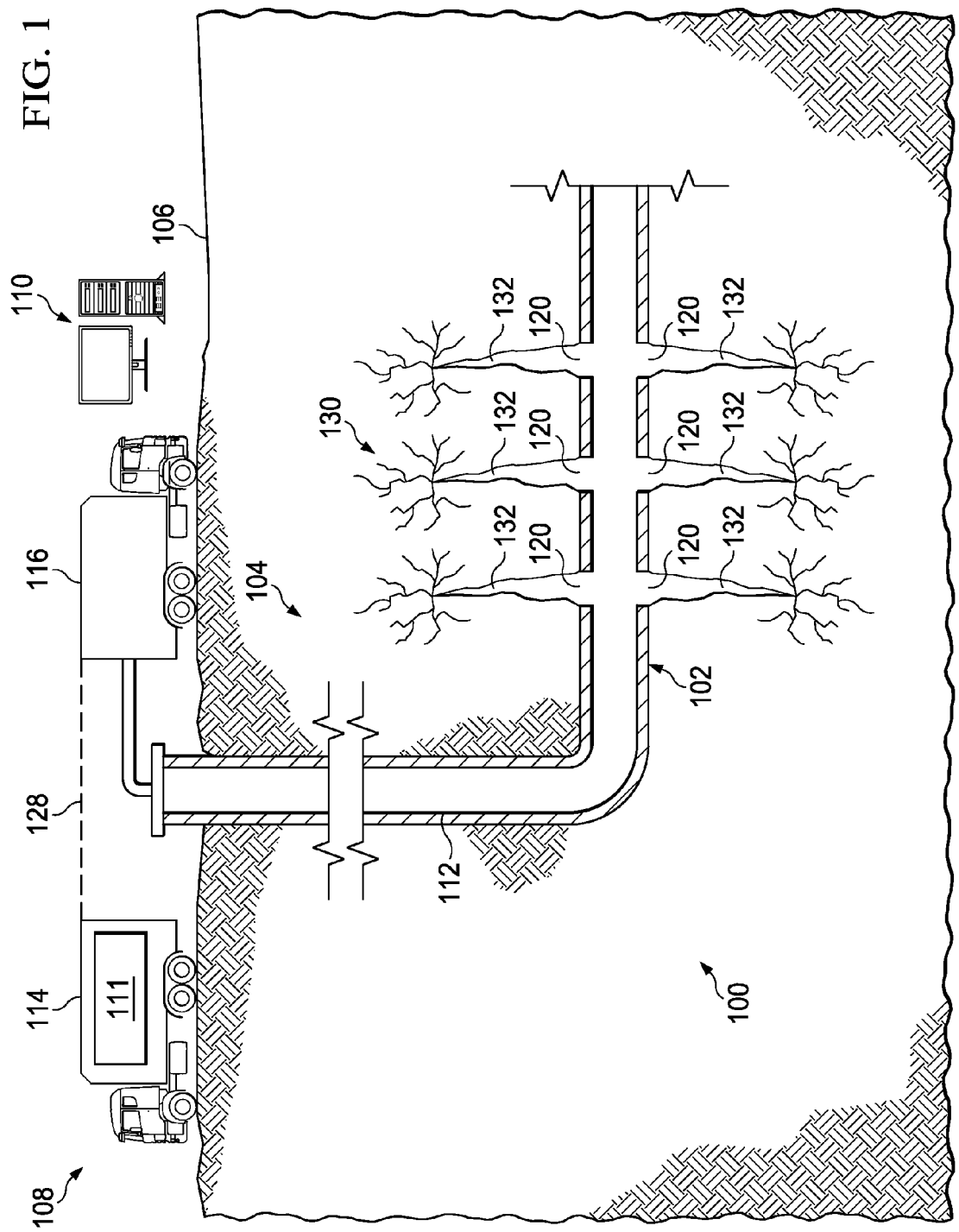
FIG. 1 is a schematic diagram of an example well system.

FIG. 1 is a diagram of an example well system 100 and a computing subsystem 110. The example well system 100 includes a wellbore 102 in a subterranean region 104 beneath the ground surface 106. The example wellbore 102 shown in FIG. 1 includes a horizontal wellbore. However, a well system may include any combination of horizontal, vertical, slant, curved, or other wellbore orientations. The well system 100 can include one or more additional treatment wells, observation wells, or other types of wells.

The computing subsystem 110 can include one or more computing devices or systems located at the wellbore 102 or other locations. The computing subsystem 110 or any of its components can be located apart from the other components shown in FIG. 1. For example, the computing subsystem 110 can be located at a data processing center, a computing facility, or another suitable location. The well system 100 can include additional or different features, and the features of the well system can be arranged as shown in FIG. 1 or in another configuration.

The example subterranean region 104 may include a reservoir that contains hydrocarbon resources, such as oil, natural gas, or others. For example, the subterranean region 104 may include all or part of a rock formation (e.g., shale, coal, sandstone, granite, or others) that contain natural gas. The subterranean region 104 may include naturally fractured rock or natural rock formations that are not fractured to any significant degree. The subterranean region 104 may include tight gas formations that include low permeability rock (e.g., shale, coal, or others).

The example well system 100 shown in FIG. 1 includes an injection system 108. The injection system 108 can be used to perform an injection treatment, whereby fluid is injected into the subterranean region 104 through the wellbore 102. In some instances, the injection treatment fractures part of a rock formation or other materials in the subterranean region 104. In such examples, fracturing the rock may increase the surface area of the formation, which may increase the rate at which the formation conducts fluid resources to the wellbore 102.

The example injection system 108 can inject treatment fluid into the subterranean region 104 from the wellbore 102. For example, a fracture treatment can be applied at a single fluid injection location or at multiple fluid injection locations in a subterranean zone, and the fluid may be injected over a single time period or over multiple different time periods. In some instances, a fracture treatment can use multiple different fluid injection locations in a single wellbore, multiple fluid injection locations in multiple different wellbores, or any suitable combination. Moreover, the fracture treatment can inject fluid through any suitable type of wellbore, such as, for example, vertical wellbores, slant wellbores, horizontal wellbores, curved wellbores, or combinations of these and others.

The example injection system 108 includes instrument trucks 114, pump trucks 116, and an injection treatment control subsystem 111. The injection system 108 may apply injection treatments that include, for example, a multi-stage fracturing treatment, a single-stage fracture treatment, a mini-fracture test treatment, a follow-on fracture treatment, a re-fracture treatment, a final fracture treatment, other types of fracture treatments, or a combination of these. The injection system 108 may inject fluid into the formation above, at or below a fracture initiation pressure for the formation; above, at or below a fracture closure pressure for the formation; or at another fluid pressure.

The pump trucks 116 can include mobile vehicles, immobile installations, skids, hoses, tubes, fluid tanks, fluid reservoirs, pumps, valves, mixers, or other types of structures and equipment. The example pump trucks 116 shown in FIG. 1 can supply treatment fluid or other materials for the injection treatment. The example pump trucks 116 can communicate treatment fluids into the wellbore 102 at or near the level of the ground surface 106. The treatment fluids can be communicated through the wellbore 102 from the ground surface 106 level by a conduit installed in the wellbore 102. The conduit 112 may include casing cemented to the wall of the wellbore 102. In some implementations, all or a portion of the wellbore 102 may be left open, without casing. The conduit 112 may include a working string, coiled tubing, sectioned pipe, or other types of conduit.

The instrument trucks 114 can include mobile vehicles, immobile installations, or other structures. The example instrument trucks 114 shown in FIG. 1 include an injection treatment control subsystem 111 that controls or monitors the injection treatment applied by the injection system 108. The communication links 128 may allow the instrument trucks 114 to communicate with the pump trucks 116, or other equipment at the ground surface 106. Additional communication links may allow the instrument trucks 114 to communicate with sensors or data collection apparatus in the well system 100, remote systems, other well systems, equipment installed in the wellbore 102 or other devices and equipment. In some implementations, communication links allow the instrument trucks 114 to communicate with the computing subsystem 110, which may run simulations and provide simulation data. The well system 100 can include multiple uncoupled communication links or a network of coupled communication links. The communication links can include wired or wireless communications systems, or combinations.

The injection system 108 may also include surface and down-hole sensors to measure pressure, rate, temperature or other parameters of treatment or production. For example, the injection system 108 may include pressure meters or other equipment that measure the pressure of fluids in the wellbore 102 at or near the ground surface 106 level or at other locations. The injection system 108 may include pump controls or other types of controls for starting, stopping, increasing, decreasing or otherwise controlling pumping as well as controls for selecting or otherwise controlling fluids pumped during the injection treatment. The injection treatment control subsystem 111 may communicate with such equipment to monitor and control the injection treatment.

The example injection treatment control subsystem 111 shown in FIG. 1 controls operation of the injection system 108. The injection treatment control subsystem 111 may include data processing equipment, communication equipment, or other systems that control injection treatments applied to the subterranean region 104 through the wellbore 102. The injection treatment control subsystem 111 may be communicably linked to the computing subsystem 110, which may calculate, select, or optimize fracture treatment parameters for initialization, propagation, or opening fractures in the subterranean region 104. The injection treatment control subsystem 111 may receive, generate or modify an injection treatment plan (e.g., a pumping schedule) that specifies parameters of an injection treatment to be applied to the subterranean region 104.

In the example shown in FIG. 1, an injection treatment has fractured the subterranean region 104. FIG. 1 shows examples of dominant fractures 132 formed by fluid injection through perforations 120 along the wellbore 102. Generally, the fractures can include fractures of any type, number, length, shape, geometry or aperture. Fractures can extend in any direction or orientation, and they may be formed at multiple stages or intervals, at different times or simultaneously. The example dominant fractures 132 shown in FIG. 1 extend through natural fracture networks 130. Generally, fractures may extend through naturally fractured rock, regions of un-fractured rock, or both. The injected fracturing fluid can flow from the dominant fractures 132, into the rock matrix, into the natural fracture networks 130, or in other locations in the subterranean region 104. The injected fracturing fluid can, in some instances, dilate or propagate the natural fractures or other pre-existing fractures in the rock formation.

In some implementations, the computing subsystem 110 can simulate fluid flow in the well system 100. For example, the computing subsystem 110 can include flow models for simulating fluid flow in or between various locations of fluid flow in the well system, such as, for example, the wellbore 102, the perforations 120, the conduit 112 or components thereof, the dominant fractures 132, the natural fracture networks 130, the rock media in the subterranean region 104, or a combination of these and others. The flow models can model the flow of incompressible fluids (e.g., liquids), compressible fluids (e.g., gases), or a combination multiple fluid phases. The flow models can also model the flow of miscible fluids, immiscible fluids, or composite fluids comprised of multiple fluids. In some instances, the flow models can model flow in one, two, or three spatial dimensions. The flow models can include nonlinear systems of differential or partial differential equations. The computing subsystem 110 can generate nodes or a mesh for use in the flow models or simulations. The computing subsystem 110 can use the flow models to predict, describe, or otherwise analyze the dynamic behavior of fluid in the well system 100.

The computing subsystem 110 can perform simulations before, during, or after the injection treatment. In some implementations, the injection treatment control subsystem 111 controls the injection treatment based on simulations performed by the computing subsystem 110. For example, a pumping schedule or other aspects of a fracture treatment plan can be generated in advance based on simulations performed by the computing subsystem 110. As another example, the injection treatment control subsystem 111 can modify, update, or generate a fracture treatment plan based on simulations performed by the computing subsystem 110 in real time during the injection system.

In some cases, the simulations are based on data obtained from the well system 100. For example, pressure meters, flow monitors, microseismic equipment, tiltmeters, or other equipment can perform measurements before, during, or after an injection treatment; and the computing subsystem 110 can simulate fluid flow based on the measured data. In some cases, the injection treatment control subsystem 111 can select or modify (e.g., increase or decrease) fluid pressures, fluid densities, fluid viscosities, fluid compositions, and other control parameters based on data provided by the simulations. In some instances, data provided by the simulations can be displayed in real time during the injection treatment, for example, to an engineer or other operator of the well system 100.

Some of the techniques and operations described herein may be implemented by a one or more computing systems configured to provide the functionality described. In various instances, a computing system may include any of various types of devices, including, but not limited to, personal computer systems, desktop computers, laptops, notebooks, mainframe computer systems, handheld computers, workstations, tablets, application servers, computer clusters, distributed computing systems, storage devices, or any type of computing or electronic device.

Figure 2:
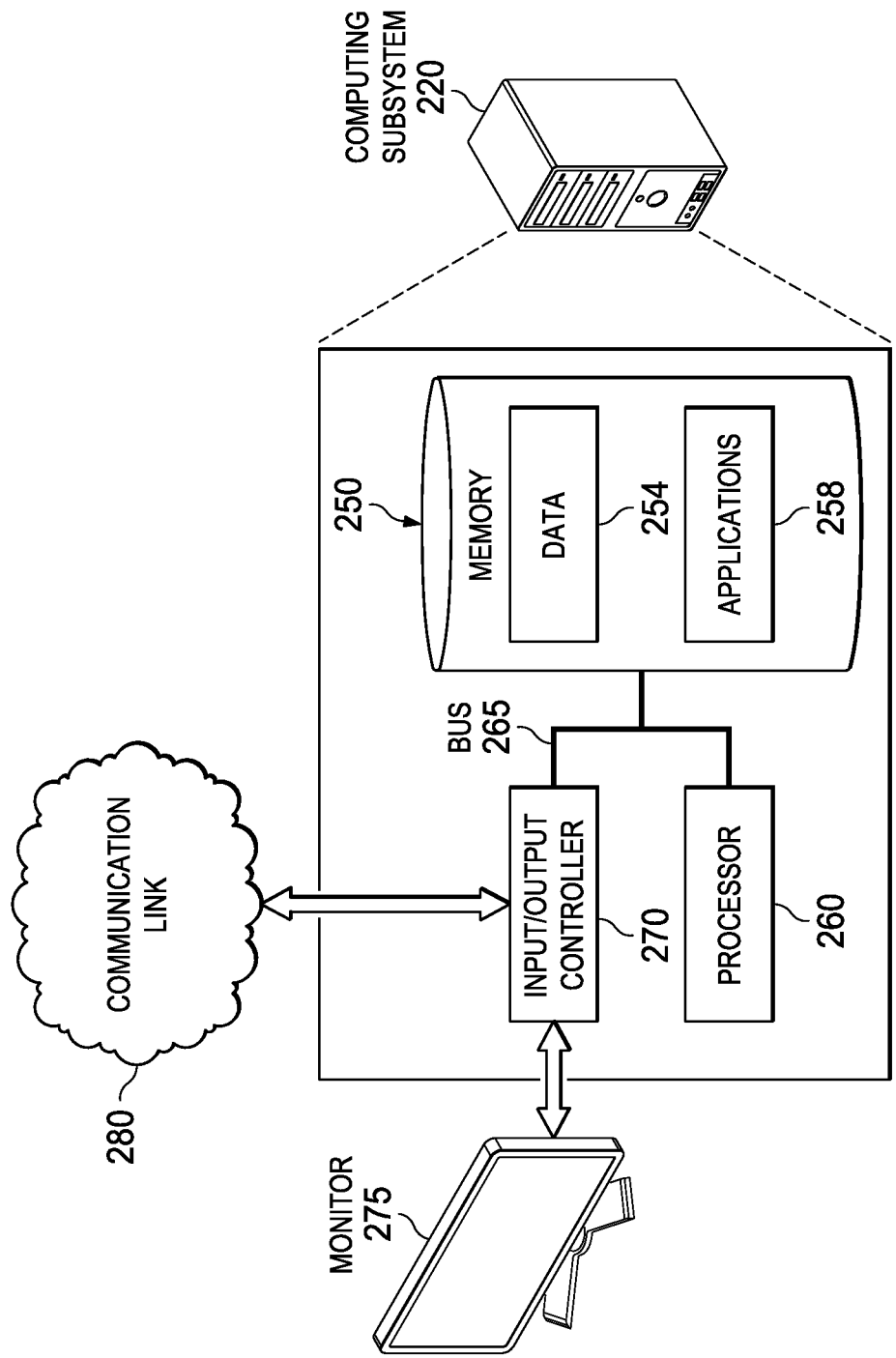
FIG. 2 is a schematic diagram of an example computing system.

FIG. 2 is a diagram of an example computing system 200. The example computing system 200 can operate as the example computing subsystem 110 shown in FIG. 1, or it may operate in another manner. For example, the computing system 200 can be located at or near one or more wells of a well system or at a remote location apart from a well system. All or part of the computing system 200 may operate independent of a well system or well system components. The example computing system 200 includes a memory 250, a processor 260, and input/output controllers 270 communicably coupled by a bus 265. The memory 250 can include, for example, a random access memory (RAM), a storage device (e.g., a writable read-only memory (ROM) or others), a hard disk, or another type of storage medium. The computing system 200 can be preprogrammed or it can be programmed (and reprogrammed) by loading a program from another source (e.g., from a CD-ROM, from another computer device through a data network, or in another manner). In some examples, the input/output controller 270 is coupled to input/output devices (e.g. a monitor 275, a mouse, a keyboard, or other input/output devices) and to a communication link 280. The input/output devices can receive or transmit data in analog or digital form over communication links such as a serial link, a wireless link (e.g. infrared, radio frequency, or others), a parallel link, or another type of link.

The communication link 280 can include any type of communication channel, connector, data communication network, or other link. For example, the communication link 280 can include a wireless or a wired network, a Local Area Network (LAN), a Wide Area Network (WAN), a private network, a public network (such as the Internet), a WiFi network, a network that includes a satellite link, or another type of data communication network.

The memory 250 can store instructions (e.g., computer code) associated with an operating system, computer applications, and other resources. The memory 250 can also store application data and data objects that can be interpreted by one or more applications or virtual machines running on the computing system 200. As shown in FIG. 2, the example memory 250 includes data 254 and applications 258. The data 254 can include treatment data, geological data, fracture data, fluid data, or any other appropriate data. The applications 258 can include flow models, fracture treatment simulation software, reservoir simulation software, or other types of applications. In some implementations, a memory of a computing device includes additional or different data, application, models, or other information.

In some instances, the data 254 include treatment data relating to fracture treatment plans. For example the treatment data can indicate a pumping schedule, parameters of a previous injection treatment, parameters of a future injection treatment, or parameters of a proposed injection treatment. Such parameters may include information on flow rates, flow volumes, slurry concentrations, fluid compositions, injection locations, injection times, or other parameters.

In some instances, the data 254 include geological data relating to geological properties of a subterranean region. For example, the geological data may include information on wellbores, completions, or information on other attributes of the subterranean region. In some cases, the geological data includes information on the lithology, fluid content, stress profile (e.g., stress anisotropy, maximum and minimum horizontal stresses), pressure profile, spatial extent, or other attributes of one or more rock formations in the subterranean zone. The geological data can include information collected from well logs, rock samples, outcroppings, microseismic imaging, or other data sources.

In some instances, the data 254 include fracture data relating to fractures in the subterranean region. The fracture data may identify the locations, sizes, shapes, and other properties of fractures in a model of a subterranean zone. The fracture data can include information on natural fractures, hydraulically-induced fractures, or any other type of discontinuity in the subterranean region. The fracture data can include fracture planes calculated from microseismic data or other information. For each fracture plane, the fracture data can include information (e.g., strike angle, dip angle, etc.) identifying an orientation of the fracture, information identifying a shape (e.g., curvature, aperture, etc.) of the fracture, information identifying boundaries of the fracture, or other information.

In some instances, the data 254 include fluid data relating to well system fluids. The fluid data may identify types of fluids, fluid properties, thermodynamic conditions, and other information related to well system fluids. The fluid data can include flow models for compressible or incompressible fluid flow. The fluid data can also include flow models for miscible or immiscible fluid mixtures, including composite fluids comprised of multiple fluids. For example, the fluid data can include systems of governing equations (e.g., Navier-Stokes equation, continuity equation, etc.) that represent fluid flow generally or fluid flow under certain types of conditions. In some cases, the governing flow equations define a nonlinear system of equations. The fluid data can include data related to native fluids that naturally reside in a subterranean region, treatment fluids to be injected into the subterranean region, proppants, hydraulic fluids that operate well system tools, or other fluids that may or may not be related to a well system.

The applications 258 can include software applications, scripts, programs, functions, executables, or other modules that are interpreted or executed by the processor 260. For example, the applications 258 can include a fluid flow simulation module, a hydraulic fracture simulation module, a reservoir simulation module, or another other type of simulator. The applications 258 may include machine-readable instructions for performing one or more of the operations related to FIGS. 3-8. For example, the applications 258 can include modules or algorithms for modeling fluid flow in a wellbore. The applications 258 may include machine-readable instructions for generating a user interface or a plot, for example, illustrating fluid flow or fluid properties. The applications 258 can receive input data, such as treatment data, geological data, fracture data, fluid data, or other types of input data, from the memory 250, from another local source, or from one or more remote sources (e.g., via the communication link 280). The applications 258 can generate output data and store the output data in the memory 250, in another local medium, or in one or more remote devices (e.g., by sending the output data via the communication link 280).

The processor 260 can execute instructions, for example, to generate output data based on data inputs. For example, the processor 260 can run the applications 258 by executing or interpreting the software, scripts, programs, functions, executables, or other modules contained in the applications 258. The processor 260 may perform one or more of the operations related to FIGS. 3-8. The input data received by the processor 260 or the output data generated by the processor 260 can include any of the treatment data, the geological data, the fracture data, the fluid data, or any other data.

Figure 3:
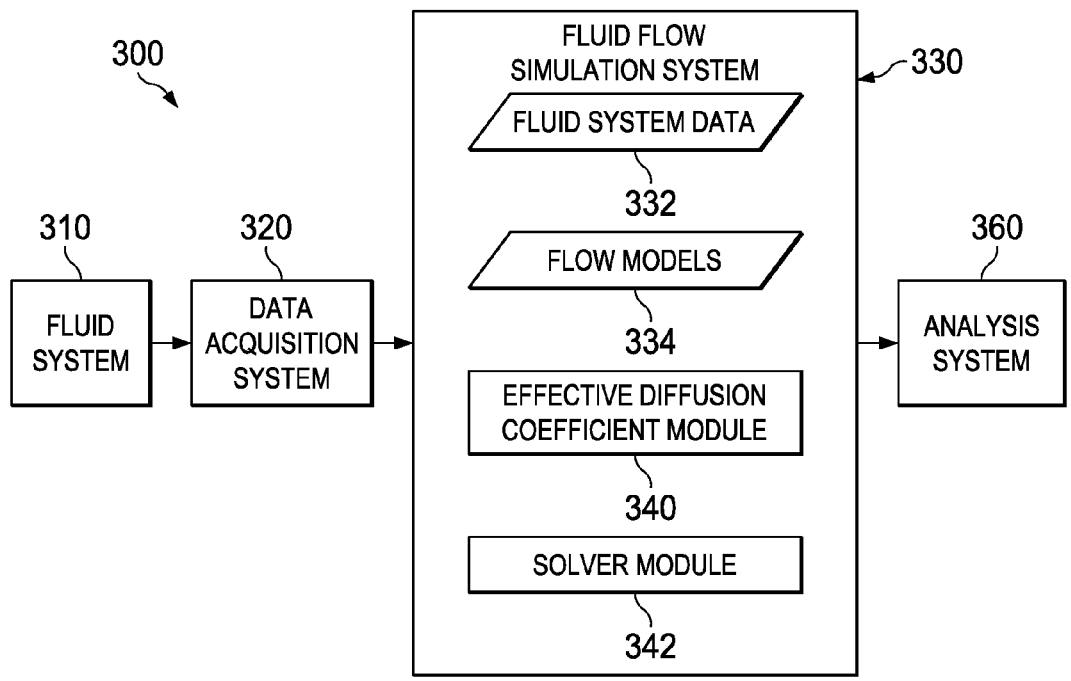
FIG. 3 is a diagram of an example system architecture.

FIG. 3 is a diagram of an example system architecture 300. The example system architecture 300 can be used to model physical phenomena related to a well system environment. For example, the architecture 300 can be used to model fluid flow in an injection treatment of the subterranean region 104 shown in FIG. 1. In some instances, the architecture 300 is used to model fluid flow and other aspects of an injection treatment or other activities in a well system. In some cases, the architecture 300 is used to model fluid flow within or between one or more wellbores, wellbore conduits, wellbore tools, wellbore perforations, reservoir rock media, reservoir fractures (e.g., fractures in a complex fracture network, in a dominant bi-wing fracture extending from a wellbore, in a natural fracture network, in hydraulically-induced fractures, etc.), or combinations of these and other types of flow paths in a well system environment.

The example architecture 300 shown in FIG. 3 includes a fluid system 310, a data acquisition system 320, a fluid flow simulation system 330, and an analysis system 360. The architecture 300 can include additional or different components or subsystems, and the example components shown in FIG. 3 can be combined, integrated, divided, or configured in another manner. For example, the fluid flow simulation system 330 and the analysis system 360 can be subcomponents of an integrated computing system (e.g., the computing system 200 shown in FIG. 2) or multiple computing systems; or the data acquisition system 320 can be integrated with the fluid system 310. As another example, the fluid flow simulation system 330 or the analysis system 360, or both, can be implemented in a computing system that operates independent of the fluid system 310 or the data acquisition system 320.

The example fluid system 310 can include any physical system where fluid flow or other fluid phenomena occur. The fluid system 310 can represent a well system environment (e.g., the well system 100 shown in FIG. 1) or a subset of well system components or subsystems (e.g., the injection system 108 shown in FIG. 1). The fluid system 310 can include the physical reservoir rock in a subterranean reservoir (e.g., the subterranean region 104 shown in FIG. 1), fractures or a fracture network in the reservoir rock, one or more downhole systems installed in a wellbore, or a combination of them.

The data acquisition system 320 can include systems or hardware that obtain data from the fluid system 310. For example, the data acquisition system 320 can include flow sensors, pressure sensors, temperature sensors, and other types of measurement devices. The data acquisition system 320 can include communication and data storage systems that store, transfer, manipulate, or otherwise manage the information obtained from the fluid system 310.

The fluid flow simulation system 330 can include one or more computer systems or computer-implemented programs that simulate fluid flow. The fluid flow simulation system 330 can receive information related to the fluid system 310 and simulate fluid flow and other fluid phenomena that occur in the fluid system 310. For example, the fluid flow simulation system 330 can calculate flow velocities, pressures, fluid concentrations, or other aspects of fluid flow based on data from the data acquisition system 320 or another source.

The example fluid flow simulation system 330 includes fluid system data 332, flow models 334, an effective diffusion coefficient module 340, and a solver 342. The fluid flow simulation system can include additional or different features, and the features of a fluid flow simulation system 330 can be configured to operate in another manner. The modules of the fluid flow simulation system 330 can include hardware modules, software modules, or other types of modules. In some cases, the modules can be integrated with each other or with other system components. In some example implementations, the fluid flow simulation system 330 can be implemented as software running on a computing system, and the modules of the fluid flow simulation system 330 can be implemented as software functions or routines that are executed by the computing system.

The fluid system data 332 can include any information related to the fluid system 310 or another fluid system. For example, the fluid system data 332 can indicate physical properties (e.g., geometry, cross-sectional areas, surface properties, etc.) of one or more flow paths in the fluid system 310, material properties (e.g., density, viscosity, Reynolds number, etc.) of one or more fluids in the fluid system 310, thermodynamic data (e.g., fluid pressures, fluid temperatures, fluid flow rates, etc.) measured at one or more locations in the fluid system 310, and other types of information. The fluid system data 332 can include information received from the data acquisition system 320 and other sources.

The flow models 334 can include any information or modules that can be used to simulate fluid flow. The flow models 334 can include governing equations, spatial and temporal discretization data, or other information. In some examples, the flow models 334 include governing flow equations, such as, for example, the Navier-Stokes equation or related approximations of the Navier-Stokes equation, diffusion-convection equations, conservation equations, continuity equations, or other types of flow equations. As an example, the flow models 334 may include one or more of the equations below; or the flow models 334 may include additional or different governing flow equations.

As shown in FIG. 3, the fluid flow simulation system 330 can also include an effective diffusion coefficient module 340. The effective diffusion coefficient module 340 can include any information or modules that can be used to model fluid displacement in a fluid flow model. For example, the effective diffusion coefficient module 340 can model fluid displacement between two miscible fluids or between two immiscible fluids. The effective diffusion coefficient module 340 can also model parameters or features of fluid displacement in a flow path. For example, the effective diffusion coefficient module 340 can model the volume of the composite fluid comprising the two fluids, such as the length of a mixing zone. In some instances, the effective diffusion coefficient module 340 includes a fluid displacement model based on a difference between the densities of two fluids, a difference between the viscosities of two fluids, or both. The effective diffusion coefficient module 340 can include a one-dimensional flow model.

The solver 342 can include any information or modules that can be used to solve a system of equations. For example, the solver 342 can be a direct solver or another type of solver. In some implementations, the solver 342 receives inputs from the other components of the fluid flow simulation system 330. For example, the inputs can include the discretized governing flow equations, information from effective diffusion coefficient module 340, the fluid system data 332, or any other information. The inputs can also include data generated or reported from a separate simulation or model. The solver 342 can generate a numerical solution for a variable of interest based on the inputs. The solution can be generated for some or all of the grid points in a discretized spatial domain. For example, the solver 342 may calculate values of fluid velocity, fluid pressure, fluid concentration, or another variable over a spatial domain; the values can be calculated for an individual time step or multiple time steps.

The analysis system 360 can include any systems, components, or modules that analyze, process, use, or access the simulation data generated by the fluid flow simulation system 330. For example, the analysis system 360 can be a real time analysis system that displays or otherwise presents fluid data (e.g., to a field engineer, etc.) during an injection treatment. In some cases, the analysis system 360 includes other simulators or a simulation manager that use the fluid simulation data to simulate other aspects of a well system. For example, the analysis system 360 can be a fracture simulation suite that simulates fracture propagation based on the simulated fluid flow data generated by the fluid flow simulation system 330. As another example, the analysis system 360 can be a reservoir simulation suite that simulates fluid migration in a reservoir based on the simulated fluid flow data generated by the fluid flow simulation system 330.

Figure 4:
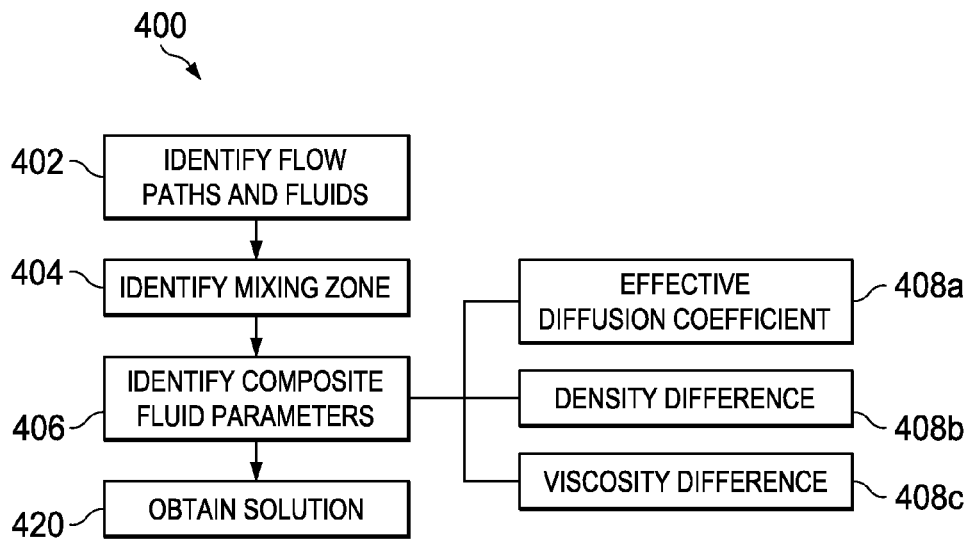
FIG. 4 is a flow chart showing an example technique for modeling fluid flow in a well system environment.

FIG. 4 is a flow chart showing an example process 400 for simulating fluid flow in a well system environment. All or part of the example process 400 may be computer-implemented, for example, using the features and attributes of the example computing system 200 shown in FIG. 2 or other computing systems. The process 400, individual operations of the process 400, or groups of operations may be iterated or performed in parallel, in series, or in another manner. In some cases, the process 400 may include the same, additional, fewer, or different operations performed in the same or a different order.

The example process 400 can be used to simulate the flow of various fluids and fluid mixtures. In some cases, the process 400 is used to simulate one or more well system fluids, proppants, or fluid mixtures. Here, the term "well system fluid" is used broadly to encompass a wide variety of fluids that may be found in or near, or may be used in connection with, a well system. Well system fluids can include one or more native fluids that reside in a subterranean region (e.g., brine, oil, natural gas, etc.), one or more fluids that have been or will be injected into a subterranean region (e.g., fracturing fluids, treatment fluids, etc.), one or more fluids that have been or will be communicated within a wellbore or within one or more tools installed in the well bore (e.g., drilling fluids, hydraulic fluids, etc.), and other types of fluids. The example process 400 can also simulate multiple types of fluid flowing within the same system. For example, process 400 can simulate fluid displacement of two fluids within a wellbore.

The example process 400 can simulate fluid flow based on a fluid flow model. For example, the process 400 can use the example one-dimensional models described with respect to FIGS. 5-8, or the process 400 can use another type of flow model. The flow model can include governing equations and associated variables.

At 402, flow paths and fluids are identified. In some cases, the flow paths are identified as flow paths in a wellbore, in a fracture or rock matrix in a subterranean rock formation, or other types of flow paths. Identifying the flow paths can include generating a discretized representation of the flow paths. Identifying the flow paths can include identifying properties of the flow paths such as length, width, geometry, composition, intersections, or other properties. Identifying the fluids can include identifying fluid types, fluid composition, fluid properties, or other information. The fluids can be identified as certain fluids in the identified flow paths. Fluid characteristics such as miscibility, density, or viscosity can be identified. In some cases, each of the identified fluids resides in a distinct domain along a flow path.

At 404, a mixing zone is identified. The mixing zone can be a region or volume in a flow path where two or more fluids meet, for example, at an interface or fluid front. The fluids in the mixing zone can include miscible or immiscible fluids that form a composite fluid; the composite fluid can have distinct fluid properties, which are based, for example, on the different properties of the constituent fluids. The composite fluid in the mixing zone can have a characteristic length or other properties. In some implementations, multiple mixing zones can be identified.

At 406, composite fluid parameters are identified. The composite fluid parameters can include parameters that describe a composite fluid comprised of two or more fluids. The composite fluid can include a solution (e.g., a homogeneous or non-homogeneous solution) of miscible fluids. The composite fluid can also include a mixture of immiscible fluids or a fluid front domain between two immiscible fluids. The composite fluid parameters can be based on the fluids identified at 402.

The composite fluid parameters can include an effective diffusion coefficient 408a, a density difference 408b, or a viscosity difference 408c. The effective diffusion coefficient 408a can describe diffusive fluid effects associated with the composite fluid, such as surface diffusion, molecular diffusion, fingering diffusion, and other effects. In some implementations, the effective diffusion coefficient 408a is based on the density difference 408b or the viscosity difference 408c. The density difference 408b can include one or more parameters based on a difference between the densities of fluids in the composite fluid. The viscosity difference 408c can include one or more parameters based on a difference between the viscosities of fluids in the composite fluid.

At 420, a solution is obtained. The solution can be obtained based on a set of conservation equations, effective diffusion coefficient equations, discretized governing flow equations, or other equations. In some implementations, the equations are solved numerically. For example, an iterative method such as Newton's method can be used to solve the equations and obtain the solution. The solution can indicate fluid properties such as concentration, velocity, or pressure. The solution can also indicate properties of the mixing zone, such as the length of the mixing zone or the concentration of fluids in the mixing zone. The solution can also indicate properties of fluid interaction, such as the location of the front of the displacing fluid in miscible fluid displacement.

Figure 5:
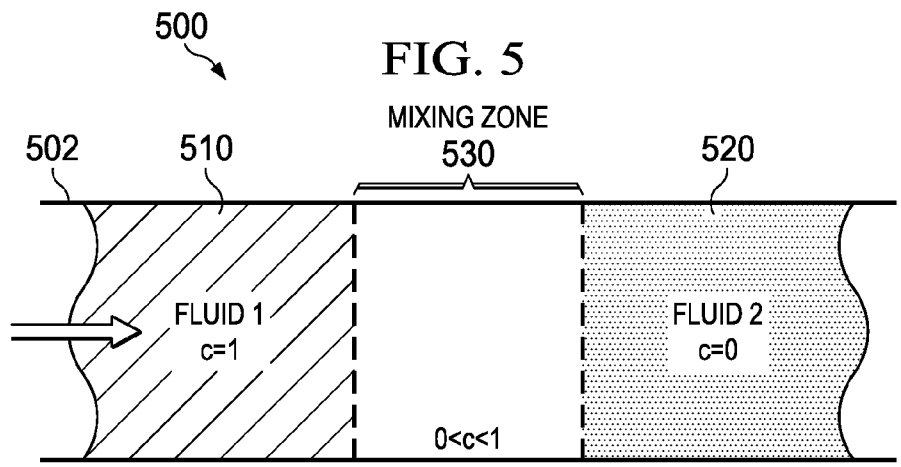
FIG. 5 is a diagram showing an example of miscible fluids in a wellbore.
Figure 6A:
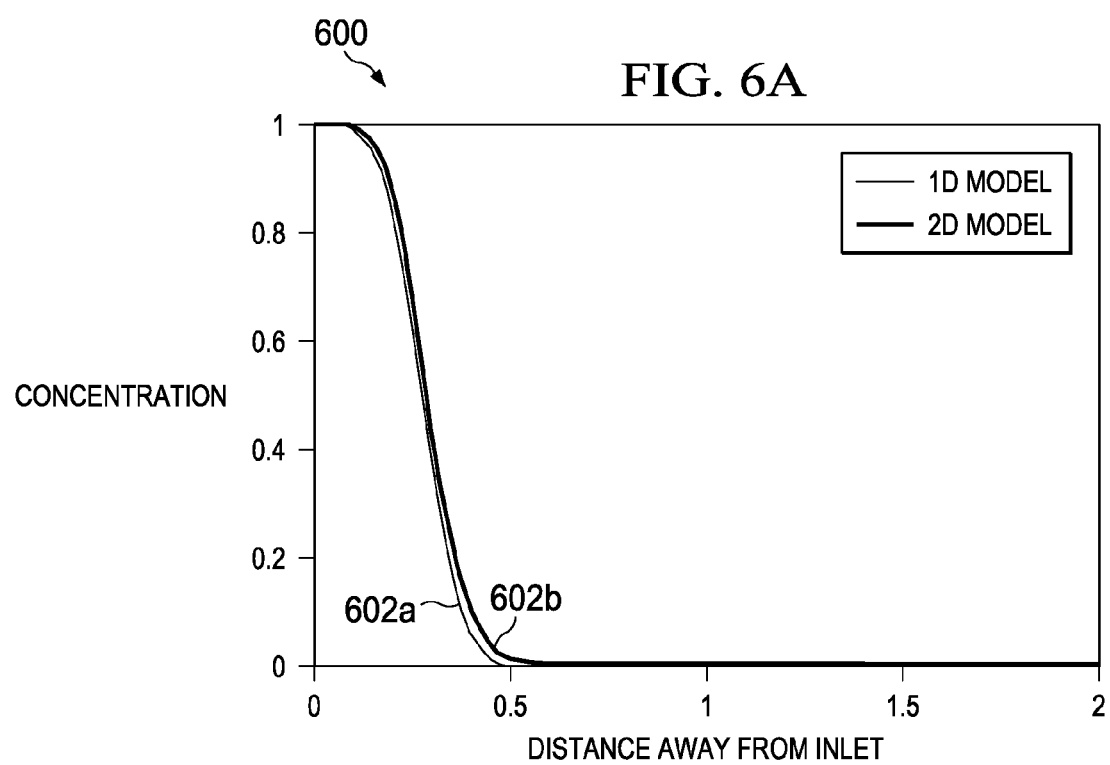
Figure 6B:
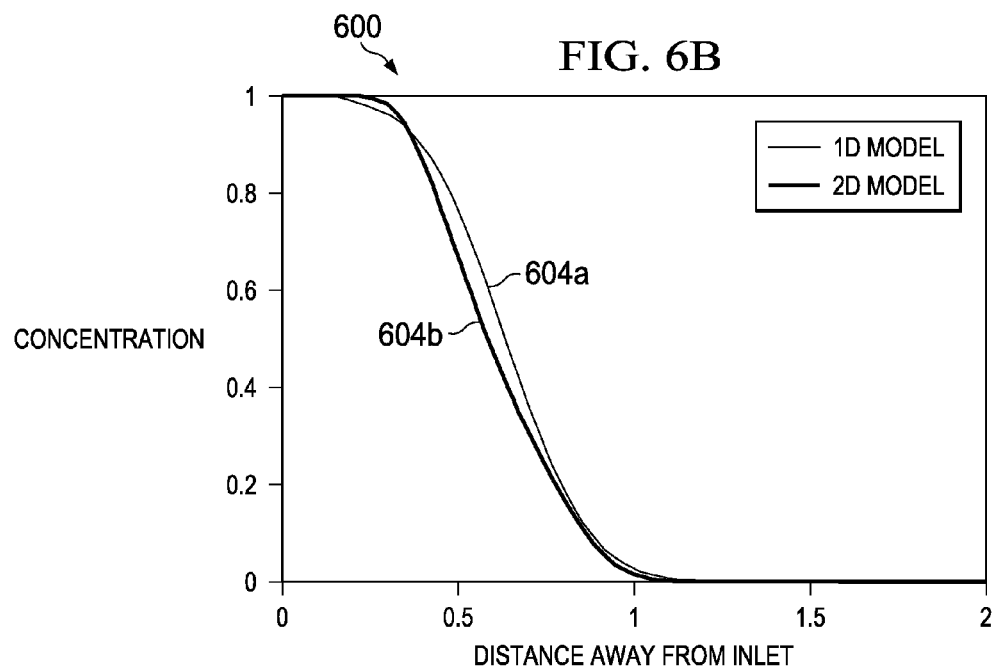
Figure 6C:
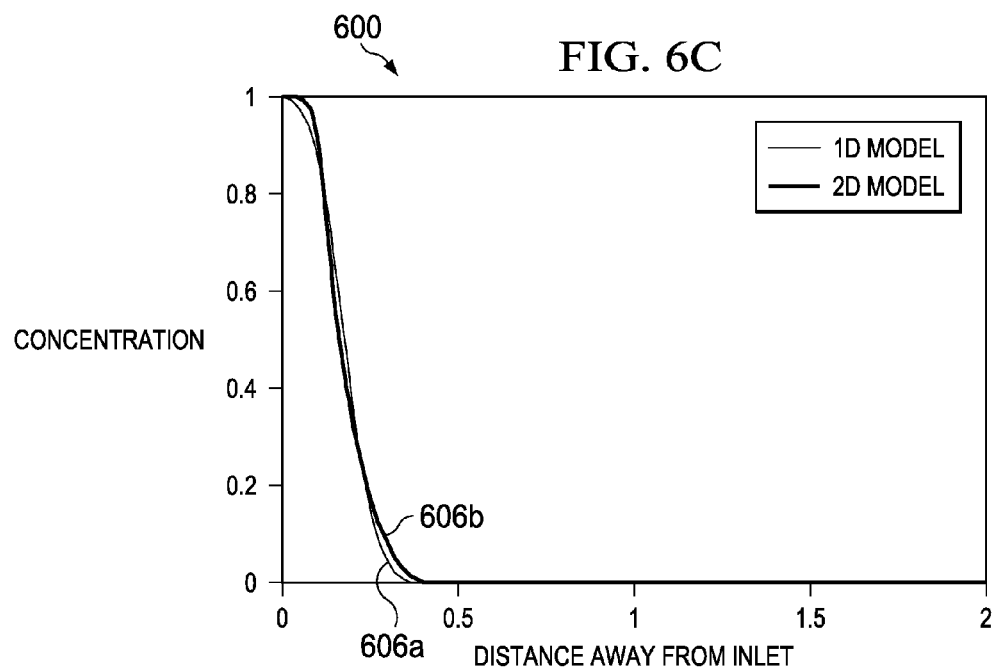

FIG. 5 shows an example schematic diagram 500 of miscible fluid displacement in a fluid channel 502. FIG. 5 depicts a Fluid 1 (510) displacing another Fluid 2 (520) in a fluid channel 502 (e.g., a wellbore or another type of flow path). In this example, Fluid 1 and Fluid 2 are miscible fluids with one or more distinct physical properties. For example, Fluid 1 can be described by a viscosity $\mu_1$ and a density $\rho_1$ and Fluid 2 by a viscosity $\mu_2$ and a density $\rho_2$, where $\mu_1 \neq \mu_2$ or $\rho_1 \neq \rho_2$. The region between the bulk Fluid 1 and the bulk Fluid 2, where the two fluids interact and mix can be described as a mixing zone 530. The mixing zone 530 is the region where some proportion of both Fluid 1 and Fluid 2 is present. The fluid present in the mixing zone 530 can be a composite of Fluid 1 and Fluid 2. In some cases, the mixing zone 530 can be described by a characteristic length.

Some example one-dimensional miscible fluid displacement models can be mathematically represented as convection-diffusion equation, where an effective diffusion coefficient is introduced to take into account the effects on the fluid displacement from convection, advection, viscosity difference and density difference. The one-dimensional model can describe fluid interaction behavior as values along the flow path. The example one-dimensional model can include one or more of example equations (1)-(14).

Example equations (1)-(3) describe the miscible fluid displacement through an overall mass conservation equation and a modified convection-diffusion equation. In equations (1) -(3), the variation of density $\rho$ and viscosity $\mu$ with the fluid concentration c can be specified, and then the fluid continuity and modified convection-diffusion equation of the concentration field can be formulated so as to integrate the cross-section averaged fluid velocity $\mu$ and the cross-section averaged fluid concentration c.

$$\rho = (\rho_1 - \rho_2)c + \rho_2 \tag{1}$$

$$\frac{\partial \rho}{\partial t} + \frac{\partial}{\partial x}(\rho u) = 0 \tag{2}$$

$$\frac{\partial c}{\partial t} + \frac{\partial}{\partial x}(\lambda u c) = \frac{\partial}{\partial x}\left(D_{e,m}\frac{\partial c}{\partial x}\right) \tag{3}$$

In equations (1)-(3), $\mu$ represents the cross-section averaged fluid velocity, and the scalar variable c represents the local volume concentration of the injected fluid as the cross-section averaged fluid concentration. For example, a region with only Fluid 1 will have a concentration c=1, whereas a region with only Fluid 2 will have a concentration c=0. In the mixing zone 530, the fluid is a composite of both Fluid 1 and Fluid 2, and thus has a concentration c described by one or more values of 0<c<1.

Equation (1) describes the overall composite fluid density $\rho$ in terms of the density of Fluid 1 ($\rho_1$) and the density of Fluid 2 ($\rho_2$) and the cross-section averaged fluid density c. Equation (2) is an equation for the overall mass continuity of both Fluid 1 and Fluid 2. Equation (3) is an example convection-diffusion equation that describes the displacement of Fluid 1 into Fluid 2. The diffusive term on the right-hand-side of equation (3) describes the diffusion of the fluids in terms of concentration c and an effective miscible diffusion constant $D_{e,m}$. The effective miscible diffusion constant $D_{e,m}$ is a single diffusive term describing multiple diffusion contributions from both Fluid 1 and Fluid 2, including density differences and viscosity differences. The second term of the right-hand-side of equation (3) describes the convection of the fluids in terms of a retarding convective factor $\lambda$. The retarding convective factor $\lambda$ is additional factor in the convection term that can account for friction-like effects of the interaction between the fluids and the sidewalls of the flow path.

The effective miscible diffusion coefficient $D_{e,m}$ can include a contribution from molecular diffusion ($D_m$) and a contribution from fingering diffusion ($D_f$), as shown in equation (4):

$$D_{e,m} = D_m + D_f \tag{4}$$

When fluids interact and mix, each fluid can form fingerlike projections into the other fluid near the fluid interface, known as fingering. The fingering diffusion $D_f$ is a factor that describes fingering effects during fluid displacement and interaction. The fingering effects can be described by the fingering diffusion factor $D_f$ given in equation (5):

$$D_f = \left(D_d + D_\mu \frac{\mu_2 - \mu_1}{\mu_2 + \mu_1} + D_\rho \frac{\rho_2 - \rho_1}{\rho_2 + \rho_1}\right) UW. \tag{5}$$

The fingering diffusion $D_f$ factor given by equation (5) includes contributions from dispersion $D_d$, the viscosity difference $D_\mu$ and the density difference $D_\rho$. The dispersion factor $D_d$ can be represented by a function $g_d$ of the Péclet number (Pe) given by the following equation:

$$D_d = g_d(Pe) \equiv \omega Pe. \tag{6}$$

In equation (6), $\omega$ can be a constant value, a variable that is computed by a model, or another type of value. The Péclet number Pe is a dimensionless ratio describing proportions of convection and diffusion in a fluid mixture and is given by:

$$Pe = \frac{UW}{D_m}. \tag{7}$$

In equation (7), U represents the average velocity of the injected Fluid 1, W represents the width of the fluid channel x02, and $D_m$ represents the molecular diffusion coefficient of the injected Fluid 1.

In equation (5), the viscosity difference $D_\mu$ can be represented by a function $g_\mu$ of the viscosities of each fluid ($\mu_1, \mu_2$) and the Schmidt number (Sc). For example, $D_\mu$ can be described by the following equation:

$$D_\mu = g_\mu(\mu_1, \mu_2, Sc) \equiv \gamma Sc\left(1 - \frac{\mu_2}{\mu_1 + \mu_2}\right). \tag{8}$$

In equation (8), $\gamma$ can be a constant value, a variable that is computed by a model, or another type of value. The Schmidt number (Sc) describes the proportion of momentum diffusion to mass diffusion in a fluid or fluid mixture and can be given by:

$$Sc = \frac{\mu_1 + \mu_2}{\rho_1 + \rho_2} D_m. \tag{9}$$

In equation (5), The density difference $D_\rho$ can be represented by a function $g_\rho$ of the densities of each fluid ($\rho_1, \rho_2$) and the Reynolds number (Re), and can be given by the following equation:

$$D_\rho = g_\rho(\rho_1, \rho_2, Re) \equiv \kappa Re\left(1 - \frac{\rho_1}{\rho_1 + \rho_2}\right). \quad (10)$$

In equation (10), $\kappa$ can be a constant value, a variable that is computed by a model, or another type of value. The Reynolds number (Re) describes a ratio of inertial forces to viscous forces in a fluid or fluid mixture, and can be given by:

$$Re = \frac{\rho_1 + \rho_2}{\mu_1 + \mu_2} UW. \quad (11)$$

As an example, values for constants $\alpha_1, \alpha_2, \alpha_3, \alpha, \beta, \omega, \gamma, \kappa$, and f are given below for fluid displacement of two miscible fluids in a 2D channel with a width W=0.1 m. The constants have been incorporated into the expressions for $D_d$, $D_\mu$, and $D_\rho$. The example values are given for the ranges $0.1 \leq Pe \leq 600$, $100 \leq Re \leq 600$, and $0.5 \leq Sc \leq 1000$. Other values and expressions can be used in other cases.

The example dispersion $D_d$ is given by:

$$D_d = \frac{Pe}{8 \times 192}, \quad (12)$$

for which $\omega = 1/(8 \times 192) \approx 0.00065$. The example viscosity difference $D_\mu$ is given by:

$$D_\mu = \frac{Sc}{8 \times 192}\left(1 - \frac{\mu_2}{\mu_1 + \mu_2}\right). \quad (13)$$

for which $\gamma = 1/(8 \times 192) \approx 0.00065$. The example density difference $D_\rho$ is given by:

$$D_\rho = \frac{Re}{32 \times 192}\left(1 - \frac{\rho_1}{\rho_1 + \rho_2}\right), \quad (14)$$

for which $\kappa = 1/(32 \times 192) \approx 0.00016$.

A one-dimensional fluid flow model for miscible fluids can account for a fluid displacement process that is dominated by dispersion when the Péclet number is large, and includes contributions from the viscosity difference and density difference representing the penetration of the fluid. The contribution of the viscosity difference $D_\mu$ to convective mixing and diffusive mixing is qualitatively captured by the sign of $(\mu_2 - \mu_1)/(\mu_1 + \mu_2)$ in equation (5). Instability can result when a more viscous fluid is displaced by a less viscous one, as the less viscous fluid has the greater mobility. Thus, a less viscous fluid displacing a more viscous one (i.e., $\mu_2 > \mu_1$) can create a larger length of the mixing zone. Conversely, a more viscous fluid displacing a less viscous one (i.e., $\mu_1 > \mu_2$) can create a shorter length of the mixing zone. The contribution of density difference to convective mixing and diffusive mixing is qualitatively captured by the sign of $(\rho_1 - \rho_2)/(\rho_1 + \rho_2)$ in equation (5). When a heavier fluid displaces a light one (i.e., $\rho_1 > \rho_2$), the heavier fluid can generate larger momentum to drive the fluid movement so as to create a larger mixing zone. Thus, the model can capture certain situations in which the moving front of the Fluid 1 extends further with a larger length of mixing zone 530.

FIGS. 6A, 6B, 6C, and 6D show example computed results for miscible fluid flow in a channel using a one-dimensional model and using a two-dimensional model. FIGS. 6A-6D show comparisons between the example one-dimensional model described with respect to FIG. 5 and a two-dimensional model. The one-dimensional model includes the example equations (1)-(11) to calculate fluid flow properties. The two-dimensional model solves the full Navier-Stokes equations in two spatial dimensions. The two-dimensional model was simulated using COMSOL Multiphysics version 4.3b, which is a commercially-available computational fluid dynamics (CFD) software module available from Comsol, Inc.

FIGS. 6A, 6B, 6C, and 6D each show the concentration c on the y-axis versus the distance from the inlet on the x-axis. The calculations from the one-dimensional model are shown as curves 602a, 604a, 606a, and 608a in FIGS. 6A, 6B, 6C, and 6D respectively. The calculations from the two-dimensional model are shown as curves 602b, 604b, 606b, and 608b in FIGS. 6A, 6B, 6C, and 6D respectively. The calculations are shown at a time t=300 s. The calculations for FIG. 6A use values of U=$1.0 \times 10^{-3}$ m/s, $\rho_1 = \rho_2 = 1000$ kg/m$^3$, $\mu_1 = \mu_2 = 1.0 \times 10^{-3}$ Pa·s, and $D_m = 1.0 \times 10^{-5}$ m$^2$/s. The calculations for FIG. 6B use values of U=$2.0 \times 10^{-3}$ m/s, $\rho_1 = \rho_2 = 1000$ kg/m$^3$, $\mu_1 = \mu_2 = 1.0 \times 10^{-3}$ Pa·s, and $D_m = 1.0 \times 10^{-6}$ m$^2$/s. The calculations for FIG. 6C use values of U=$1.0 \times 10^{-3}$ m/s, $\rho_1 = \rho_2 = 1000$ kg/m$^3$, $\mu_1 = 0.3 \times 10^{-3}$ Pa·s, $\mu_2 = 0.7 \times 10^{-3}$ Pa·s, and $D_m = 1.0 \times 10^{-6}$ m$^2$/s. The calculations for FIG. 6D use values of U=$1.0 \times 10^{-3}$ m/s, $\rho_1 = 400$ kg/m$^3$, $\rho_2 = 600$ kg/m$^3$, $\mu_1 = \mu_2 = 1.0 \times 10^{-3}$ Pa·s, and $D_m = 1.0 \times 10^{-6}$ m$^2$/s.

The data shown in FIGS. 6A-6D provide an example of the accuracy of calculations in the example one-dimensional model for miscible fluid displacement compared against a two-dimensional model. FIGS. 6A-6D show that the one-dimensional effective diffusion coefficient model can describe miscible fluid interaction, particularly with regard to the length of the mixing zone. Similarly accurate results are obtained for situations with fluids with different properties, such as different fluid densities or different fluid viscosities.

FIG. 7 shows an example schematic diagram 700 of immiscible fluid displacement in a fluid channel 702. FIG. 7 depicts a Fluid 3 (710) displacing another Fluid 4 (720) in a fluid channel 702 (e.g., a wellbore or another type of fluid channel). In this example, Fluid 3 and Fluid 4 are immiscible fluids (e.g. oil and water) that form an inhomogeneous composite fluid in the mixing zone 703. The fluids have distinct physical properties. For example, Fluid 3 can be described by a viscosity $\mu_3$ and a density $\rho_3$ and Fluid 4 by a viscosity 4 and a density $\rho_4$, where $\mu_3 \neq \mu_4$ or $\rho_3 \neq \rho_4$. The region between the bulk Fluid 3 and the bulk Fluid 4 where the two fluids interact and mix can be described by mixing zone 730. The mixing zone 730 is the region where some proportion of both Fluid 3 and Fluid 4 is present. In some cases, the mixing zone 730 can be described by a characteristic length.

Example equations (15)-(24) describe immiscible fluid displacement through an overall mass conservation equation and a modified convection-diffusion equation. In the following example model equations, $\mu$ represents the cross-section averaged fluid velocity, and the scalar variable c represents the local volume concentration of the injected fluid as the cross-section averaged fluid concentration. The two fluids are assumed to be fully immiscible subject to a constant surface tension $\sigma$, and the fluid-fluid interface is assumed to have a capillary thickness $\epsilon$.

$$\rho = (\rho_3 - \rho_4)c + \rho_4 \quad (15)$$

$$\frac{\partial \rho}{\partial t} + \frac{\partial}{\partial x}(\rho u) = 0 \quad (16)$$

$$\phi = 2c - 1 \quad (17)$$

$$\frac{\partial c}{\partial t} + \frac{\partial}{\partial x}(\lambda u c) = \frac{\partial}{\partial x}\left(D_{e,i}\frac{\partial}{\partial x}\left(\phi(\phi-1) - \varepsilon^2\frac{\partial^2 \phi}{\partial x^2}\right)\right) \quad (18)$$

Equation (15) describes the overall fluid density $\rho$ in terms of the cross-section averaged fluid density c. Equation (16) is an equation for mass continuity. Equation (17) rescales the concentration c to a value of $\phi$ such that $-1 \leq \phi \leq 1$. Equation (18) is an example convection-diffusion equation that describes the displacement of Fluid 3 into Fluid 4 in terms of an effective immiscible diffusion constant $D_{e,i}$ and a retarding convective factor $\lambda$.

The effective immiscible diffusive constant $D_{e,i}$ can be described by:

$$D_{e,i} = D_s + \left(D_d + D_\mu \frac{\mu_4 - \mu_3}{\mu_4 + \mu_3} + D_\rho \frac{\rho_4 - \rho_3}{\rho_4 + \rho_3}\right) UW \quad (19)$$

In equation (19), W represents the width of the channel. The viscosity difference $D_\mu$ and density difference $D_\rho$ can be defined for Fluid 3 and Fluid 4 analogous to equations (13) and (14):

$$D_\mu \equiv \gamma Sc\left(1 - \frac{\mu_4}{\mu_3 + \mu_4}\right), \quad (20)$$

$$D_\rho \equiv \kappa Re\left(1 - \frac{\rho_3}{\rho_3 + \rho_4}\right). \quad (21)$$

The surface diffusivity in equation (19) is represented by $D_s$ and given by:

$$D_s = \frac{0.5 \zeta \gamma_m}{\varepsilon^2}. \quad (22)$$

In equation (22), $\zeta$ represents the energy of mixing and $\gamma_m$ represents the interface mobility. In equation (19), $D_d$ represents the dispersion. The dispersion $D_d$ can be represented by a function $h_d$ of the Capillary number Ca:

$$D_d = h_d(Ca) = \zeta Ca. \quad (23)$$

In equation (23), $\zeta$ can be a constant value, a variable that is computed by a model, or another type of value. The Capillary number Ca is described by:

$$Ca = \frac{\mu_3 + \mu_4}{\sigma} U, \quad (24)$$

where U is the average velocity of the injected Fluid 3, and $\sigma$ is the surface tension at the interface.

As an example, an expression for $D_d$ is given below:

$$D_d = 6.5 \times 10^{-5} Ca \quad (25)$$

Other parameters such as $D_\mu$ and $D_\rho$ can be optimized via comparison with corresponding scenarios in two-dimensional simulations. For example, $D_\mu$ and $D_\rho$ can be set to zero in immiscible fluid displacement scenarios for which $Re \geq 10000$.

Some example one-dimensional models for immiscible fluid flow can account for enhancement of the fluid displacement by surface diffusive mixing and convection. The length of the mixing zone and axial front of the fluid-fluid interface can depend on the competition between the magnitude of Capillary number Ca, the fluid viscosity $\mu$ and density $\rho$, and the interface mobility $\gamma_m$. The fluid viscosity and the surface tension can control the diffusive process for the mixing zone length, while the surface tension, capillary thickness, and mobility can govern the fluid-fluid interface front. Specifically, the fluid displacement process can be dominated by the convection when the surface tension number is large, and can be corrected by the contributions from the viscosity difference and density difference representing the penetration of the fluid. The contribution of viscosity difference to the axial front and length of the mixing zone is qualitatively captured by the sign of $(\mu_4-\mu_3)/(\mu_3+\mu_4)$ in equation (19). Instability can result when a more viscous fluid is displaced by a less viscous one, as the less viscous fluid has the greater mobility. Thus, a less viscous fluid displacing a more viscous one (i.e., $\mu_4 > \mu_3$) can create a larger length of the mixing zone. Conversely, a more viscous fluid displacing a less viscous one can create a shorter length of the mixing zone. The contribution of density difference to convective mixing and diffusive mixing is qualitatively captured by the sign of $(\rho_3-\rho_4)/(\rho_3+\rho_4)$ in equation (19). When a heavier fluid displaces a light one (i.e., $\rho_3 > \rho_4$), the heavier fluid can generate larger momentum to drive the fluid movement so as to create a larger mixing zone length. Thus, the model captures the moving front of the Fluid 3 extending further and the length of mixing zone being larger.

FIGS. 8A and 8B show example computed results for immiscible fluid flow in a channel using a one-dimensional model and using a two-dimensional model. FIG. 8A and FIG. 8B show comparisons between the example one-dimensional model described with respect to FIG. 7 and an example two-dimensional model. The one-dimensional model includes the example equations (15)-(24) to calculate fluid flow properties. The two-dimensional model solves the full Navier-Stokes equations in two spatial dimensions. The two-dimensional model was simulated using COMSOL Multiphysics version 4.3b, which is a commercially-available computational fluid dynamics (CFD) software module available from Comsol, Inc.

FIG. 8A is a plot 800 showing example computed results 802a and 802b for air displacement by injected water in a channel. In FIG. 8A, the y-axis is the volume fraction of the water, and the x-axis is the distance along the channel from the point of injection. The calculations using the one-dimensional model are shown as curve 802a, and the calculations using the two-dimensional model are shown as curve 802b. The calculations are shown at a time $t=1.0$ s. The calculations use values of $U=0.1$ m/s, $\gamma=1.0 \times 10^{-3}$ m$^4$/(N·s), and $\epsilon=0.01$ M.

FIG. 8B is a plot 810 showing example computed results 812a and 812b for motor oil displacement by injected water in a channel. In FIG. 8B, the y-axis is the volume fraction of the water, and the x-axis is the distance along the channel from the point of injection. The calculations using the one-dimensional model are shown as curve 812a, and the calculations using the two-dimensional model are shown as curve 812b. The calculations are shown at a time $t=2.0$ s. The calculations use values of $U=0.1$ m/s, $\gamma=1.0 \times 10^{-3}$ m$^4$/(N·s), and $\epsilon=0.01$ M.

The data shown in FIGS. 8A and 8B provide an example of the accuracy of calculations in an example one-dimensional immiscible fluid displacement model compared against a two-dimensional model. The plots show that the one-dimensional effective diffusion coefficient model can represent immiscible fluid interaction, particularly with regard to the length of the mixing zone and the front of the displacing fluid. Similarly accurate results are obtained for situations with fluids with different properties, such as different fluid densities or different fluid viscosities.

Some embodiments of subject matter and operations described in this specification can be implemented in digital electronic circuitry, or in computer software, firmware, or hardware, including the structures disclosed in this specification and their structural equivalents, or in combinations of one or more of them. Some embodiments of subject matter described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read-only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of examples have been described. Nevertheless, it will be understood that various modifications can be made. Accordingly, other implementations are within the scope of the following claims.

The invention claimed is:

1. A flow modeling method comprising:
    receiving, from a data acquisition system, properties of a flow path in a well system environment and properties of a first fluid and a second fluid in the flow path;

generating a one-dimensional flow model that models flow of the first fluid and the second fluid in the flow path in the well system environment by integrating governing flow equations over a cross-section of the flow path in a two or more dimensions based on the properties of the flow path and the properties of the first fluid and the second fluid in the flow path, the governing flow equations based on Navier-Stokes equations that account for spatial and temporal variations of the properties of the first fluid and the second fluid, the one-dimensional flow model comprising an effective diffusion coefficient model for a composite fluid volume comprising the first and second fluids, the effective diffusion coefficient model based on a difference between respective densities of the first fluid and the second fluid, the one-dimensional flow model further comprising a retarding convective factor that accounts for friction-like effects of interaction between the first fluid and the second fluids and sidewalls of the flow path;

wherein the one-dimensional flow model models fluid flow in a subterranean region during an injection treatment applied to the subterranean region, the first fluid comprising an injection fluid, and the second fluid comprising a native fluid that resides in the subterranean region;

on a computer system, operating the one-dimensional flow model based on a cross-section averaged fluid velocity, a cross-section averaged fluid concentration, the effective diffusion coefficient model, and a Reynolds number calculated based on the first fluid's viscosity, the second fluid's viscosity, the first fluid's density, the second fluid's density, the first fluid's average velocity, and a width of the flow path;

wherein the first and second fluids comprise immiscible fluids, and operating the effective diffusion coefficient model comprising calculating an effective diffusion coefficient $D_e$ for the composite fluid volume based on the equation:

$$D_e = D_s + \left(D_d + D_\mu \frac{\mu_2 - \mu_1}{\mu_2 + \mu_1} + D_\rho \frac{\rho_2 - \rho_1}{\rho_2 + \rho_1}\right)UW,$$

where $D_s$ represents surface diffusivity, $D_d$ represents dispersion, $D_\mu$ represents a viscosity difference factor, $D_\rho$ represents a density difference factor, $\mu_1$ represents the first fluid's viscosity, $\mu_2$ represents the second fluid's viscosity, $\rho_1$ represents the first fluid's density, $\rho_2$ represents the second fluid's density, U represents the first fluid's average velocity, and W represents a width of the flow path; and controlling the injection treatment based on results of operating the one-dimensional flow model during the injection treatment.

2. The method of claim 1, wherein the effective diffusion coefficient model is based on a difference between respective viscosities of the first fluid and the second fluid.

3. The method of claim 1, wherein the first and second fluids comprise immiscible fluids, and operating the one-dimensional flow model simulates the first fluid displacing the second fluid in the flow path.

4. The method of claim 1, wherein the first and second fluids comprise miscible fluids, and operating the one-dimensional flow model simulates the first fluid displacing the second fluid in the flow path.

5. The method of claim 1, wherein the composite fluid volume comprises a mixing zone of the first fluid and the second fluid in the flow path, and the effective diffusion coefficient model is based on a length of the mixing zone.

6. The method of claim 1, wherein the one-dimensional flow model models fluid flow in a wellbore in a subterranean region, and operating the one-dimensional flow model simulates the first fluid displacing the second fluid in the wellbore.

7. The method of claim 1, wherein the viscosity difference factor $D_\mu$ is calculated based on the equation:

$$D_\mu = \gamma Sc\left(1 - \frac{\mu_2}{\mu_1 + \mu_2}\right),$$

wherein $\gamma$ is a viscosity difference coefficient and the Schmidt number Sc is calculated based on:

$$Sc = \frac{\mu_1 + \mu_2}{\rho_1 + \rho_2} D_m,$$

where D represents a molecular diffusion factor for the first fluid.

8. The method of claim 1, wherein the density difference factor $D_\rho$ is calculated based on the equation:

$$D_\rho = \kappa Re\left(1 - \frac{\rho_1}{\rho_1 + \rho_2}\right),$$

wherein $\kappa$ is a density difference coefficient and the Reynolds number Re is calculated based on:

$$Re = \frac{\rho_1 + \rho_2}{\mu_1 + \mu_2} UW.$$

9. The method of claim 1, wherein the one-dimensional flow model models flow of more than two fluids in the flow path in the well system environment by integrating governing flow equations over a cross-section of the flow path in a two or more dimensions based on the properties of the flow path and the properties of the more than two fluids in the flow path, the governing flow equations are based on Navier-Stokes equations that account for spatial and temporal variations of the properties of the more than two fluids.

10. A non-transitory computer-readable medium storing instructions that, when executed by a data processing apparatus, perform operations comprising:

receiving properties of a flow path in a well system environment and properties of a first fluid and a second fluid in the flow path;

generating a one-dimensional flow model that models flow of the first fluid and the second fluid in the flow path in the well system environment by integrating governing flow equations over a cross-section of the flow path in a two or more dimensions based on the properties of the flow path and the properties of the first fluid and the second fluid in the flow path, the governing flow equations based on Navier-Stokes equations that account for spatial and temporal variations of the properties of the first fluid and the second fluid, the one-dimensional flow model comprising an effective diffusion coefficient model for a composite fluid volume comprising the first and second fluids, the effective diffusion coefficient model based on a difference between respective densities of the first fluid and the second fluid, the one-dimensional flow model further comprising a retarding convective factor that accounts for friction-like effects of interaction between the first fluid and the second fluids and sidewalls of the flow path;

wherein the one-dimensional flow model models fluid flow in a subterranean region during an injection treatment applied to the subterranean region, the first fluid comprising an injection fluid, and the second fluid comprising a native fluid that resides in the subterranean region; and operating the one-dimensional flow model based on a cross-section averaged fluid velocity, a cross-section averaged fluid concentration, the effective diffusion coefficient model, and a Reynolds number calculated based on the first fluid's viscosity, the second fluid's viscosity, the first fluid's density, the second fluid's density, the first fluid's average velocity, and a width of the flow path;

wherein the first and second fluids comprise miscible fluids, and operating the effective diffusion coefficient model comprising calculating an effective diffusion coefficient $D_e$ for the composite fluid volume based on the equation:

$$D_e = D_m + D_{fi},$$

where $D_m$ represents a molecular diffusion factor for the first fluid, and $D_f$ represents a fingering diffusion factor, wherein the fingering diffusion factor is given by the equation:

$$D_f = \left(D_d + D_\mu \frac{\mu_2 - \mu_1}{\mu_2 + \mu_1} + D_\rho \frac{\rho_2 - \rho_1}{\rho_2 + \rho_1}\right)UW,$$

where $D_d$ represents dispersion, $D_\mu$ represents a viscosity difference factor, $D_\rho$ represents a density difference factor, $\mu_1$ represents the first fluid's viscosity, $\mu_2$ represents the second fluid's viscosity, $\rho_1$ represents the first fluid's density, $\rho_2$ represents the second fluid's density, U represents the first fluid's average velocity, and W represents a width of the flow path; and controlling the injection treatment based on results of operating the one-dimensional flow model during the injection treatment.

11. The computer-readable medium of claim 10, wherein the effective diffusion coefficient model is based on a difference between respective densities of the first fluid and the second fluid.

12. The computer-readable medium of claim 10, wherein the viscosity difference factor $D_\mu$ is calculated based on the equation:

$$D_\mu = \gamma Sc\left(1 - \frac{\mu_2}{\mu_1 + \mu_2}\right),$$

wherein $\gamma$ is a viscosity difference coefficient and the Schmidt number Sc is calculated based on:

$$Sc = \frac{\mu_1 + \mu_2}{\rho_1 + \rho_2} D_m.$$

13. The computer-readable medium of claim 10, wherein the density difference factor $D_\mu$ is calculated based on the equation:

$$D_\rho = \kappa Re\left(1 - \frac{\rho_1}{\rho_1 + \rho_2}\right),$$

wherein $\kappa$ is a density difference coefficient and the Reynolds number Re is calculated based on:

$$Re = \frac{\rho_1 + \rho_2}{\mu_1 + \mu_2} UW.$$

14. The computer-readable medium of claim 10, wherein the composite fluid volume comprises a mixing zone of the first fluid and the second fluid in the flow path, and the effective diffusion coefficient model is based on a length of the mixing zone.

15. A flow modeling system comprising one or more computer systems that include:

memory adapted to store a one-dimensional flow model that models flow of a first fluid and a second fluid in a flow path in a well system environment by integrating governing flow equations over a cross-section of the flow path in a two or more dimensions based on properties of the flow path and properties of the first fluid and the second fluid in the flow path, the governing flow equations based on Navier-Stokes equations that account for spatial and temporal variations of the properties of the first fluid and the second fluid, wherein the one-dimensional flow model models fluid flow in a subterranean region during an injection treatment applied to the subterranean region, the first fluid comprising an injection fluid, and the second fluid comprising a native fluid that resides in the subterranean region, the one-dimensional flow model comprising an effective diffusion coefficient model for a composite fluid volume comprising the first and second fluids, the effective diffusion coefficient model based on:

a difference between respective viscosities of the first fluid and the second fluid; and a difference between respective densities of the first fluid and the second fluid;

the one-dimensional flow model further comprising a retarding convective factor that accounts for friction-like effects of interaction between the first fluid and the second fluids and sidewalls of the flow path; and data processing apparatus adapted to access the memory and operate the one-dimensional flow model based on the effective diffusion coefficient model, a cross-section averaged fluid velocity, a cross-section averaged fluid concentration, and a Reynolds number calculated based on the first fluid's viscosity, the second fluid's viscosity, the first fluid's density, the second fluid's density, the first fluid's average velocity, and a width of the flow path;

when the first and second fluids comprise immiscible fluids, the data processing apparatus adapted to calculate an effective diffusion coefficient $D_e$ for the composite fluid volume based on the equation:

$$D_e = D_s + \left(D_d + D_\mu \frac{\mu_2 - \mu_1}{\mu_2 + \mu_1} + D_\rho \frac{\rho_2 - \rho_1}{\rho_2 + \rho_1}\right)UW,$$

where $D_s$ represents surface diffusivity, $D_d$ represents dispersion, $D_\mu$ represents a viscosity difference factor, $D_\rho$ represents a density difference factor, $\mu_1$ represents the first fluid's viscosity, $\mu_2$ represents the second fluid's viscosity, $\rho_1$ represents the first fluid's density, $\rho_2$ represents the second fluid's density, U represents the first fluid's average velocity, and W represents a width of the flow path;

when the first and second fluids comprise miscible fluids, the data processing apparatus adapted to calculate an effective diffusion coefficient $D_e$ for the composite fluid volume based on the equation:

$$D_e = D_m + D_f,$$

where $D_m$ represents a molecular diffusion factor for the first fluid, and $D_f$ represents a fingering diffusion factor, wherein the fingering diffusion factor is given by the equation:

$$D_f = \left(D_d + D_\mu \frac{\mu_2 - \mu_1}{\mu_2 + \mu_1} + D_\rho \frac{\rho_2 - \rho_1}{\rho_2 + \rho_1}\right) UW,$$

where $D_d$ represents dispersion, $D_\mu$ represents a viscosity difference factor, $D_\rho$ represents a density difference factor, $\mu_1$ represents the first fluid's viscosity, $\mu_2$ represents the second fluid's viscosity, $\rho_1$ represents the first fluid's density, $\rho_2$ represents the second fluid's density, U represents the first fluid's average velocity, and W represents a width of the flow path; and the data processing apparatus further adapted to control the injection treatment based on results of operating the one-dimensional flow model during the injection treatment.

16. The flow modeling system of claim 15, wherein the first and second fluids comprise immiscible fluids, and operating the one-dimensional flow model simulates the first fluid displacing the second fluid in the flow path.

17. The flow modeling system of claim 15, wherein the first and second fluids comprise miscible fluids, and operating the one-dimensional flow model simulates the first fluid displacing the second fluid in the flow path.

* * * * *